US007812185B2

(12) United States Patent
Burdett et al.

(10) Patent No.: US 7,812,185 B2
(45) Date of Patent: Oct. 12, 2010

(54) METATHESIS PROCESS FOR PREPARING AN ALPHA, OMEGA-FUNCTIONALIZED OLEFIN

(75) Inventors: Kenneth A. Burdett, Midland, MI (US); Morteza Mokhtarzadeh, Charleston, WV (US); Francis J. Timmers, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 504 days.

(21) Appl. No.: 11/915,794

(22) PCT Filed: Jun. 2, 2006

(86) PCT No.: PCT/US2006/021232

§ 371 (c)(1),
(2), (4) Date: Nov. 28, 2007

(87) PCT Pub. No.: WO2006/132902

PCT Pub. Date: Dec. 14, 2006

(65) Prior Publication Data

US 2008/0228017 A1    Sep. 18, 2008

Related U.S. Application Data

(60) Provisional application No. 60/687,843, filed on Jun. 6, 2005.

(51) Int. Cl.
    *C09F 7/00* (2006.01)
(52) U.S. Cl. .............................. 554/27; 564/25; 564/26
(58) Field of Classification Search ............ 554/25, 554/26, 27
    See application file for complete search history.

(56) References Cited

U.S. PATENT DOCUMENTS 3,261,879 A    7/1966    Banks (Continued)

FOREIGN PATENT DOCUMENTS

DE        3229419        10/1987

(Continued)

OTHER PUBLICATIONS

K.A. Burdett et al., Organometallics, Renewable Monomer Feedstocks via Olefin Metathesis : Fundamental Mechanistic Studies of Methyl Oleate Ethenolysis with the First-Generation Grubbs Catalyst, 2004(23), pp. 2027-2047.

(Continued)

*Primary Examiner*—Deborah D Carr

(57) ABSTRACT

A cross-metathesis process for preparing an $\alpha,\omega$-functionalized olefin, such as methyl 9-decenoate, and an $\alpha$-olefin having three or more carbon atoms, such as 1-decene. The process involves contacting in a first reaction zone an $\alpha$-functionalized internal olefin, such as methyl oleate, and an $\alpha$-olefinic monomer having three or more carbon atoms, such as 1-decene, with a first metathesis catalyst to prepare an effluent stream containing the $\alpha,\omega$-functionalized olefin, such as methyl 9-decenoate, an unfunctionalized internal olefin, such as 9-octadecene, unconverted reactant olefins, and optionally, an $\alpha,\omega$-difunctionalized internal olefinic dimer, such as dimethyl 9-octadecen-1,18-dioate; separating said effluent streams; then contacting in a second reaction zone the unfunctionalized internal olefin with ethylene in the presence of a second metathesis catalyst to obtain a second product effluent containing the $\alpha$-olefinic monomer having three or more carbon atoms; and cycling a portion of the $\alpha$-olefinic monomer stream(s) to the first zone.

25 Claims, 2 Drawing Sheets

U.S. PATENT DOCUMENTS

| | | | |
|---|---|---|---|
| 3,647,906 | A | 3/1972 | Farley |
| 5,312,940 | A | 5/1994 | Grubbs et al. |
| 5,710,298 | A | 1/1998 | Grubbs et al. |
| 6,306,988 | B1 | 10/2001 | Grubbs et al. |
| 7,176,336 | B2 | 2/2007 | Maughon at al. |
| 2003/0055262 | A1 | 3/2003 | Grubbs et al. |
| 2005/0154221 | A1 | 7/2005 | Lysenko et al. |
| 2006/0167326 | A1 | 7/2006 | Burdett et al. |

FOREIGN PATENT DOCUMENTS

| | | |
|---|---|---|
| WO | WO93/20111 | 10/1993 |
| WO | WO96/04289 | 2/1996 |
| WO | WO00/43343 | 7/2000 |
| WO | WO02/076920 | 10/2002 |
| WO | WO02/083742 | 10/2002 |
| WO | WO03/093215 | 11/2003 |
| WO | WO2004/037754 | 5/2004 |
| WO | WO2006/047105 | 5/2006 |

OTHER PUBLICATIONS

M. Sholl et al., Synthesis and Activity of a New Generation of Ruthenium-Based Olefin Metathesis Catalysts Coordinated with 1,3-Dimesityl-4,5-dihydroimidazol-2-ylidine Ligands, Organic Letters, 1999, vol. 1, No. 6, pp. 953-956.

J. Kingsbury, A Recyclable Ru-Based Metathesis Catalyst, Journal of the American Chemical Society, 1999, 121, pp. 791-799.

W.A. Hermann et al, Metal Complexes of N-Heterocyclic Carbenes-A New Structural :Principle for Catalysts in Homogeneous Catalysis, Angewandte Chemie, International Edition, 1995, 21, pp. 2371-2374.

R.R. Schrock et al., Synthesis of Molybdenum Imido Alkylidene Complexes and Some Reactions Involving Acyclic Olefins, Journal of American Chemical Society, 1990, 112, pp. 3875-3886.

European Chemical News, Plant & Design Metathesis, Getting the Balance Right, Week of Mar. 25-31, 2002, pp. 20-21.

Chem Systems, PERP Report #97/98S3, "Routes to Propylene," Feb. 2000, pp. 1-149.

Copending U.S. Appl. No. 10/503,805, Integrated Chemical Processes for Industrial Utilization of Seed Oils, filed Apr. 29, 2003, Zenon Lysenko et al.; equivalent to WO2003/093215 and US 2005/0154221.

Copending U.S. Appl. No. 10/528,472, Stabilization of Olefin Metathesis Product Mixtures, filed Sep. 26, 2003, Kenneth A. Burdett et al.; equivalent to WO2004/037754 and US 2006/0167326.

Copending U.S. Appl. No. 11/765,723, Membrane Separation of a Metathesis Reaction Mixture, filed May 1, 2008, Kenneth A. Burdett et al.; equivalent to WO2006/047105.

METATHESIS PROCESS FOR PREPARING AN ALPHA, OMEGA-FUNCTIONALIZED OLEFIN

CROSS-REFERENCE TO RELATED APPLICATIONS

This application is a 371 of International Patent Application PCT/US2006/021232, filed Jun. 2, 2006, which claims the benefit of U.S. Provisional Application Ser. No. 60/687,843, filed Jun. 6, 2005.

This invention was made with Government support under Contract No. DE-FC36-01ID141213 awarded by the Department of Energy. The Government has certain rights in this invention.

BACKGROUND OF THE INVENTION

In one aspect, this invention pertains to an olefin metathesis process wherein an α-functionalized internal olefin, such as methyl 9-octadecenoate (methyl oleate), is converted in two metathesis steps to an α,ω-functionalized olefin, such as methyl 9-decenoate, and a co-product α-olefin, such as 1-decene.

"Metathesis" generally refers to a chemical process wherein two reactant olefins, either identical or different in composition, react through double bond (C=C) scission and reforming to form one or more product olefins that are different from the reactant olefins. When the reactant olefins are identical in composition, the process is a "homo-metathesis." When the reactant olefins are different compositions, the process is a "cross-metathesis."

Cross-metathesis of α-functionalized internal olefins, such as unsaturated fatty acids or unsaturated fatty acid esters, with ethylene produces valuable α,ω-functionalized olefins and α-olefins as products, typically characterized by chain lengths intermediate between the chain lengths of the reactant olefins. As an example, methyl 9-octadecenoate (methyl oleate) can be metathesized with ethylene in the presence of a metathesis catalyst to prepare methyl 9-decenoate and 1-decene. α-Olefins, such as 1-decene, find utility in the manufacture of poly(olefin) polymers. α,ω-Unsaturated esters, such as methyl 9-decenoate, can be readily hydrolyzed to the corresponding α,ω-unsaturated acids, such as 9-decenoic acid, which find utility in thermoset polymer applications, including thermoset urethanes. Alternatively, α,ω-unsaturated acids can be converted into α,ω-epoxy acids, which find utility, for example, in the manufacture of epoxy resins.

Cross-metathesis reactions have been disclosed, for example, in WO 96/04289, wherein methyl 9-octadecenoate is metathesized with ethylene in the presence of a ruthenium catalyst to form an α,ω-unsaturated acid or ester, namely, methyl 9-decenoate, and a co-product α-olefin, namely, 1-decene. Suitable catalysts for this cross-metathesis process comprise homogeneous ruthenium catalysts including first-generation Grubbs catalysts, exemplified by bis(tricyclohexylphosphine)-benzylidene ruthenium dichloride, and second-generation Grubbs catalysts, exemplified by tricyclohexylphosphine[1,3-bis(2,4,6-trimethylphenyl)-4,5-dihydroimidazol-2-ylidene][benzylidene]ruthenium dichloride. "First-generation and second-generation Grubbs catalysts," named for their principle inventor Robert H. Grubbs, are disclosed in the following illustrative patent publications: WO 96/04289 and WO 02/083742 and references therein. First-generation and second-generation Grubbs catalysts tend to be relatively tolerant towards air, moisture, and a wide array of polar functional groups, such as acid and ester functionalities. Moreover, in metathesis processes second-generation Grubbs catalysts exhibit high catalyst turnover numbers, provided that the reactants do not include ethylene. For the purposes of this invention, "catalyst turnover number" shall refer to the number of moles of α-functionalized internal olefin converted per mole of metathesis catalyst. A "high" catalyst turnover number shall mean a turnover number of greater than about 50,000 moles of α-functionalized internal olefin converted per mole of metathesis catalyst.

Disadvantageously, for cross-metathesis with ethylene, first- and second-generation Grubbs catalysts exhibit either rapid deactivation or unacceptable catalyst turnover numbers well below 50,000. The art suggests that, in part, this resultant catalyst instability is related to the presence of a metal-methylidene intermediate complex which forms on reaction of ethylene with the metal of the metathesis catalyst, typically, ruthenium. Consequently, the skilled artisan is confronted with a task of recovering the deactivated catalyst from the homogeneous reaction mixture, and then regenerating and recycling an activated catalyst back to the metathesis reaction. Unfortunately, recovery and regeneration of Grubbs catalysts are difficult to accomplish. Accordingly, the cross-metathesis of α-functionalized internal olefins with ethylene (ethenolysis) to higher valued cross-metathesis products, such as intermediate chain α,ω-functionalized olefins and co-product α-olefins, remains far from commercialization.

It would be desirable to discover a cross-metathesis process for preparing α,ω-functionalized olefins and co-product α-olefins from an α-functionalized internal olefin in which the metathesis catalyst possesses an insensitivity to polar functional groups, such as ester or carboxylic acid substituents, on the reactant olefin(s); in which the formation of any catalyst destabilizing intermediate complex is minimized, particularly with Grubbs catalysts; and in which the catalyst turnover number and catalyst lifetime are significantly improved as compared with prior art metathesis catalysts. With those advancements, the heretofore cost-prohibitive problem of recovering, regenerating and recycling a homogeneous metathesis catalyst should be avoided. Instead, with significantly improved catalyst turnover number and catalyst lifetime, economic studies indicate that a low concentration of catalyst can be employed, and the catalyst can be simply discarded upon its eventual deactivation.

SUMMARY OF THE INVENTION

This invention provides for a novel metathesis process of preparing an α,ω-functionalized olefin and an α-olefin having three or more carbon atoms comprising:

(a) contacting in a first reaction zone an α-functionalized internal olefin and an α-olefinic monomer having three or more carbon atoms in the presence of a first metathesis catalyst under reaction conditions sufficient to prepare a first effluent stream comprising an α,ω-functionalized olefin, an unfunctionalized internal olefin, unconverted α-functionalized internal olefin, unconverted α-olefinic monomer having three or more carbon atoms, and optionally, an α,ω-difunctionalized internal olefinic dimer;

(b) introducing the first effluent stream from step (a) into a first separation zone and recovering therefrom an α,ω-functionalized olefin stream, an unfunctionalized internal olefin stream, an unconverted α-functionalized internal olefin stream, a first output α-olefinic monomer stream wherein the monomer has three or more carbon atoms, and optionally, an α,ω-difunctionalized internal olefinic dimer stream;

(c) contacting in a second reaction zone a portion of the unfunctionalized internal olefin stream with ethylene in the presence of a second metathesis catalyst under reaction conditions sufficient to prepare a second effluent stream comprising the α-olefinic monomer having three or more carbon atoms, unconverted unfunctionalized internal olefin, and unconverted ethylene;

(d) introducing the second effluent stream from step (c) into a second separation zone under conditions sufficient to obtain a second output α-olefinic monomer stream, wherein the monomer has three or more carbon atoms, an unconverted ethylene stream, and an unconverted unfunctionalized internal olefin stream; and (e) removing a portion of the first and/or second output α-olefinic monomer stream as product and cycling the balance of the first and second output α-olefinic monomer streams to the first reaction zone in step (a).

On net balance, the process of this invention consumes feeds of an α-functionalized internal olefin and ethylene and produces an α,ω-functionalized olefin and a co-product α-olefin (herein, α-olefinic monomer having three or more carbon atoms), both olefinic products of shorter chain length than the α-functionalized internal olefin (and of intermediate chain length between the α-functionalized internal olefin and ethylene). Although the process of this invention comprises two metathesis steps to form the same products that are achieved in only one step in the prior art, this present invention affords significant advantages over the prior art. First, in the process of this invention advantage can be taken of Grubbs catalysts, particularly high turnover number second-generation Grubbs catalysts, which are desirably insensitive to olefins bearing polar functional groups, such as acids and esters. Second, the process of this invention significantly advances the prior art process by uncoupling the presence of Grubbs catalyst and ethylene in one metathesis reaction zone. Such uncoupling advantageously avoids the formation of any catalyst-destabilizing complex intermediate. Specifically, in the first metathesis step of this invention, the α-functionalized internal olefin is reacted with an α-olefinic monomer having three or more carbon atoms, ethylene being excluded, in the presence of a first metathesis catalyst, preferably a Grubbs catalyst, which is relatively insensitive to the functional group. Since ethylene is not employed, higher catalyst turnover number and longer catalyst lifetime are beneficially achieved, as compared with a similar process wherein ethylene is substituted for the α-olefinic monomer having three or more carbon atoms. In the second metathesis reaction, a co-product of the first reaction, specifically, the unfunctionalized internal olefin is beneficially utilized with ethylene (ethenolysis) to produce the reactant α-olefinic monomer having three or more carbon atoms which is needed for the first metathesis step, thereby circulating and coupling the two steps. In this second metathesis step, which involves no polar functional groups, any metathesis catalyst can be employed, and ethylene-sensitive Grubbs catalysts can be avoided. The benefits and advantages of this process invention will become more apparent in the detailed description that follows.

DRAWING

DETAILED DESCRIPTION OF THE INVENTION

Figure 1:
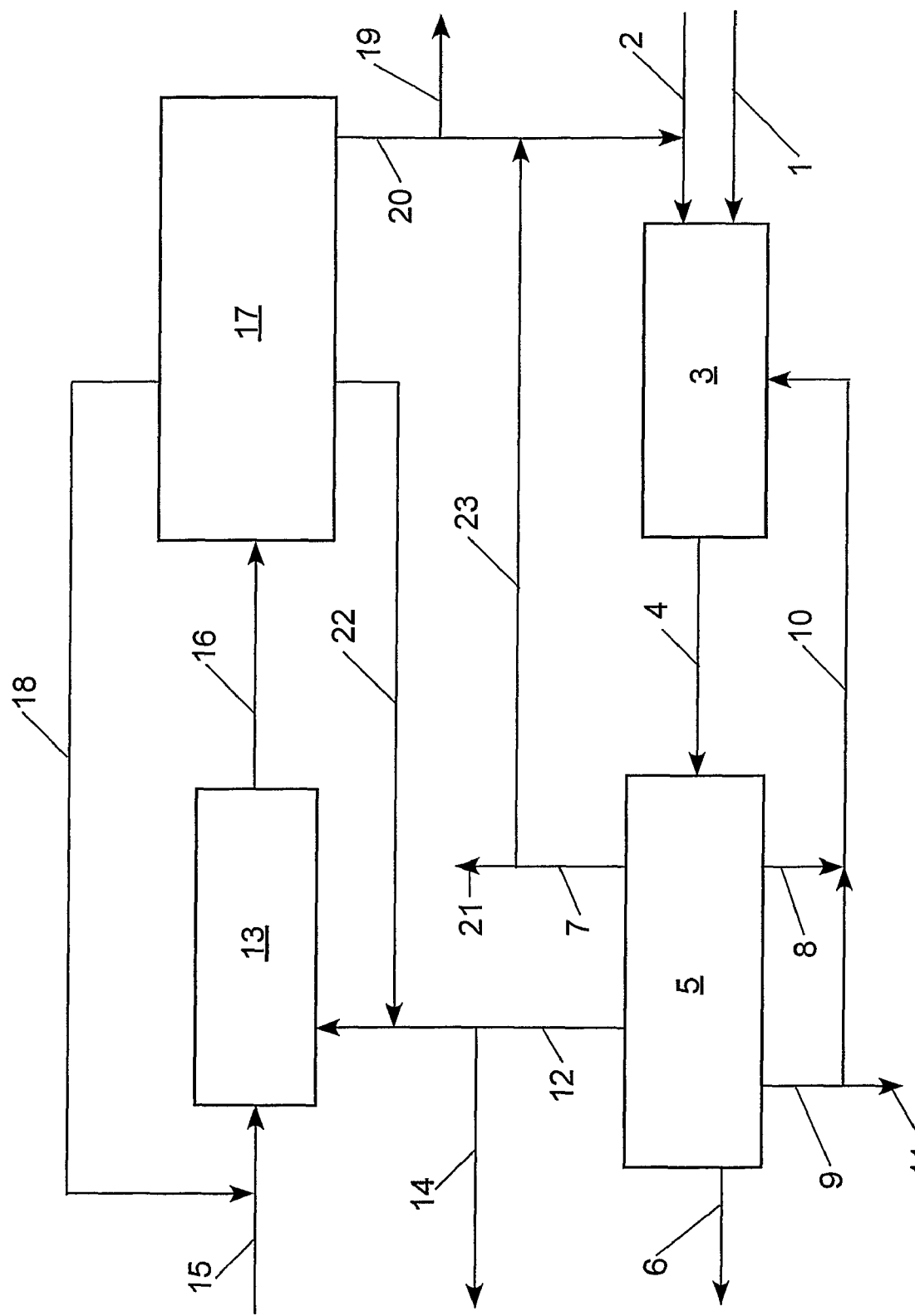
FIG. 1 illustrates a preferred embodiment of this invention for preparing an α,ω-functionalized olefin, for example, methyl 9-decenoate, and a co-product x-olefin having three or more carbon atoms, for example, 1-decene.

The invention described herein provides for a novel metathesis process of preparing an α,ω-functionalized olefin and a co-product α-olefin having three or more carbon atoms, the process comprising:

(a) contacting in a first reaction zone an α-functionalized internal olefin and an α-olefinic monomer having three or more carbon atoms in the presence of a first metathesis catalyst under reaction conditions sufficient to prepare a first effluent stream comprising an α,ω-functionalized olefin, an unfunctionalized internal olefin, unconverted α-functionalized internal olefin, unconverted α-olefinic monomer having three or more carbon atoms, and optionally, an α,ω-difunctionalized internal olefinic dimer;

(b) introducing the first effluent stream from step (a) into a first separation zone and recovering therefrom an α,ω-functionalized olefin stream, an unfunctionalized internal olefin stream, an unconverted α-functionalized internal olefin stream, a first output α-olefinic monomer stream, the monomer having three or more carbon atoms, and optionally, an α,ω-difunctionalized internal olefinic dimer stream;

(c) contacting in a second reaction zone a portion of the unfunctionalized internal olefin stream with ethylene in the presence of a second metathesis catalyst under reaction conditions sufficient to prepare a second effluent stream comprising the α-olefinic monomer having three or more carbon atoms, unconverted unfunctionalized internal olefin, and unconverted ethylene;

(d) introducing the second effluent stream from step (c) into a second separation zone under conditions sufficient to obtain a second output α-olefinic monomer stream, the monomer having three or more carbon atoms, an unconverted ethylene stream, and an unconverted unfunctionalized internal olefin stream; and (e) removing a portion of the first and/or second output α-olefinic monomer stream as product and cycling the balance of the first and second output α-olefinic monomer streams to the first reaction zone in step (a).

The unfunctionalized internal olefin produced in the process contains a chain of carbon atoms with a double bond (C=C) at an internal position along the chain (i.e., not a terminal carbon atom). The term "unfunctionalized" means that the α,ω-terminal positions consist of methyl groups that are not substituted with any further functionality. The unfunctionalized internal olefin may be further characterized as symmetrical or unsymmetrical. In the symmetrical form the carbon chains on either side of the double bond are equal in length. The symmetrical form is referred to herein as an "unfunctionalized internal olefinic dimer." In the unsymmetrical form the carbon chains on either side of the double bond are unequal in length. Depending upon the specific carbon chain lengths in the reactant α-functionalized internal olefin and the reactant α-olefin having three or more carbon atoms, the product mixture may contain one or more than one unfunctionalized internal olefin. Typically, if only one unfunctionalized internal olefin is produced, the form is symmetrical. On the other hand, if a mixture of unfunctionalized internal olefins is produced, then the mixture typically contains one symmetrical and at least one unsymmetrical internal olefin.

In a preferred embodiment, this invention provides for a process of preparing an α,ω-functionalized olefin and a co-product α-olefin having three or more carbon atoms comprising:

(a) contacting in a first reaction zone an α-functionalized internal olefin represented by the formula:

$$CH_3—(R)_w—CH=CH—(R')_{w'}—X \quad (1)$$

(wherein R, R', w, w', and X are identified hereinbelow) is contacted with an α-olefinic monomer having three or more carbon atoms represented by the formula:

$$CH_2=CH—(R)_w—CH_3 \quad (2)$$

in the presence of a first metathesis catalyst under reaction conditions sufficient to prepare a first effluent stream comprising an α,ω-functionalized olefin represented by the formula:

$$CH_2=CH—(R')_{w'}—X \quad (3)$$

an unfunctionalized internal olefinic dimer represented by the formula:

$$CH_3—(R)_w—CH=CH—(R)_w—CH_3 \quad (4)$$

unconverted α-functionalized internal olefin of formula (1), unconverted α-olefinic monomer having three or more carbon atoms of formula (2), and optionally, an α,ω-difunctionalized internal olefinic dimer represented by the formula:

$$X—(R')_{w'}—CH=CH—(R')_{w'}—X \quad (5);$$

(b) introducing the effluent stream from step (a) into a first separation zone and recovering an α,ω-functionalized olefin stream, an unfunctionalized internal olefinic dimer stream, an unconverted α-functionalized internal olefin stream, a first output α-olefinic monomer stream, the monomer having three or more carbon atoms, and optionally, an α,ω-difunctionalized internal olefinic dimer stream, each stream being represented by its respective formula shown in step (a);

(c) contacting in a second reaction zone a portion of the unfunctionalized internal olefinic dimer stream represented by formula (4) with ethylene in the presence of a second metathesis catalyst under reaction conditions sufficient to prepare a second effluent stream comprising an α-olefinic monomer having three or more carbon atoms represented by formula (2), unconverted unfunctionalized internal olefinic dimer of formula (4), and unconverted ethylene;

(d) introducing the second effluent stream from step (c) into a second separation zone under conditions sufficient to obtain a second output α-olefinic monomer stream represented by formula (2), an unconverted unfunctionalized internal olefinic dimer stream of formula (4), and an unconverted ethylene stream; and (e) removing a portion of the first and/or second output α-olefinic monomer stream as product and cycling the balance of the first and second output α-olefinic monomer streams to the first reaction zone in step (a).

In formula (1) hereinabove, R and R' are each independently selected from substituted or unsubstituted hydrocarbyl diradicals, preferably, substituted or unsubstituted aliphatic hydrocarbyl diradicals, more preferably, alkylene or alkylidene diradicals, most preferably, methylene (e.g., —CH$_2$—); w and w' are each independently a whole number ranging from 0 to about 20, preferably, from about 3 to about 12; and X is a polar functional group, preferably, a polar functional group selected from carboxylic acid, ester, formyl, and dialkylamide groups, more preferably, a C$_{1-8}$ ester group. Likewise, in formulas (2), (3), (4) and (5), each of R, R', w, w' and X is defined similarly to the respective definition set forth in formula (1), provided that each R, R', w, w', and X in formulas (2), (3), (4), and (5) is also identical to the corresponding group or number selected for formula (1).

In a more preferred embodiment, the invention provides for a continuous process of preparing methyl 9-decenoate and 1-decene comprising:

(a) contacting in a first reaction zone methyl 9-octadecenoate (methyl oleate) and 1-decene in the presence of a ruthenium metathesis catalyst under reaction conditions sufficient to prepare a first effluent stream comprising methyl 9-decenoate, 9-octadecene, unconverted methyl 9-octadecenoate, unconverted 1-decene, and optionally, dimethyl 9-octadecen-1,18-dioate;

(b) introducing the first effluent stream from step (a) into a first separation zone and recovering therefrom a methyl 9-decenoate stream, a 9-octadecene stream, an unconverted methyl 9-octadecenoate stream, a first output 1-decene stream, and optionally, a dimethyl 9-octadecen-1,18-dioate stream;

(c) contacting in a second reaction zone a portion of the 9-octadecene stream with ethylene in the presence of a heterogeneous metathesis catalyst, under reaction conditions sufficient to prepare a second effluent stream comprising 1-decene, unconverted 9-octadecene and unconverted ethylene;

(d) introducing the second effluent stream from step (c) into a second separation zone under conditions sufficient to obtain a second output 1-decene stream, an unconverted ethylene stream, and an unconverted octadecene stream; and (e) removing a portion of the first and/or second output 1-decene streams as product and cycling the balance of the first and second output 1-decene streams to the first reaction zone in step (a).

In another preferred embodiment, the invention provides for a continuous process of preparing methyl 9-decenoate and 1-octene comprising:

(a) contacting in a first reaction zone methyl 9-hexadecenoate (methyl palmitoleate) and 1-octene in the presence of a ruthenium metathesis catalyst under reaction conditions sufficient to prepare a first effluent stream comprising methyl 9-decenoate, 7-tetradecene, unconverted methyl 9-hexadecenoate, unconverted 1-octene, and optionally, dimethyl 9-octadecene-1,18-dioate;

(b) introducing the first effluent stream from step (a) into a first separation zone and recovering therefrom a methyl 9-decenoate stream, a 7-tetradecene stream, an unconverted methyl 9-hexadecenoate stream, a first output 1-octene stream, and optionally, a dimethyl 9-octadecen-1,18-dioate stream;

(c) contacting in a second reaction zone a portion of the 7-tetradecene stream with ethylene in the presence of a heterogeneous metathesis catalyst under reaction conditions sufficient to prepare a second effluent stream comprising 1-octene, unconverted 7-tetradecene, and unconverted ethylene;

(d) introducing the second effluent stream from step (c) into a second separation zone under conditions sufficient to obtain a second output 1-octene stream, an unconverted ethylene stream, and an unconverted 7-tetradecene stream; and (e) removing a portion of the first and/or second output 1-octene stream as product and cycling the balance of the first and second output 1-octene streams to the first reaction zone in step (a).

A preferred embodiment of this invention is illustrated with reference to FIG. 1. In this preferred embodiment, a feed comprising an α-functionalized internal olefin is introduced through feed line (1) into a first metathesis reactor (3). Simultaneously, a feed comprising α-olefin having three or more carbon atoms is introduced through feed line (2) into the first metathesis reactor (3). Said feed in feed line (2) may comprise a commercial start-up quantity of said α-olefin, or a recycle quantity of said α-olefin that is unconverted in said first metathesis reactor, or a quantity of said α-olefin derived as a product from the second metathesis step of this process invention, or some combination thereof. An effluent stream from first metathesis reactor (3) is transported through effluent line (4) to a first separation zone (5). In first separation zone (5) a product stream comprising α,ω-functionalized olefin is obtained as product line (6). Also, from first separation zone (5) is obtained a stream (first output) comprising unconverted α-olefin having three or more carbons atoms in product line (7). A portion of unconverted α-olefin having three or more carbon atoms in effluent line (7) may be recycled via line (23) to line (20) and into line (2) for recycle to the first metathesis reactor (3). The portion of α-olefin recycled will depend upon the stoichiometry requirements in the first metathesis reactor (3). The balance of the α-olefin having three or more carbon atoms in effluent line (7) may be bled off via bleed line (21).

Further to FIG. 1, from first separation zone (5) is obtained unconverted α-functionalized internal olefin stream in effluent line (8), and optionally, α,ω-difunctionalized internal olefinic dimer stream in effluent line (9). Unconverted α-functionalized internal olefin in effluent line (8) is transported to recycle line (10) for recycling to the first metathesis reactor (3). If the α,ω-difunctionalized internal olefinic dimer is formed, then a portion of the α,ω-difunctionalized internal olefinic dimer in effluent line (9) may be fed to recycle line (10) for recycle to the first metathesis reactor (3). The balance of the α,ω-difunctionalized internal olefinic dimer, if any, from effluent line (9) may be bled off as waste product via line (11). Again the recycle portion depends upon the amount of said product produced and the stoichiometry requirements in first metathesis reactor (3).

Further to FIG. 1, from first separation zone (5) unfunctionalized internal olefin is obtained and transported via effluent line (12) to the second metathesis reactor (13). A portion of the unfunctionalized internal olefin may be bled from transport line (12) through bleed line (14) to maintain proper stoichiometry in the second metathesis reactor. Ethylene is fed via feed line (15) to the second metathesis reactor (13) for reaction over the second metathesis catalyst. An effluent stream comprising the α-olefin monomer having three or more carbon atoms, unconverted unfunctionalized olefin, and unconverted ethylene is obtained in effluent line (16) from the second metathesis reactor (13) and fed to the second separation zone (17). A top stream comprising unreacted ethylene is obtained in effluent line (18) from the second separation zone (17) and recycled via ethylene feed line (15) to the second metathesis reactor (13). A bottoms stream comprising unconverted unfunctionalized internal olefin is obtained via bottoms stream (22) and recycled to the second metathesis reactor (13) for further ethenolysis. A stream comprising the α-olefinic monomer having three or more carbon atoms (second output stream) is obtained from the second separation zone (17) through effluent line (20), a portion of which stream is recycled as feed to the first metathesis zone (3) via line (2). The balance of the α-olefinic monomer stream is typically bled off the second separation zone (17) via bleed line (19) as product for downstream utilities and for maintaining stoichiometry in the first metathesis zone (3).

Any α-functionalized internal olefin that is capable of cross-metathesis with an α-olefin having three or more carbon atoms to form an α,ω-functionalized olefinic product may be employed in the process of this invention. As used herein, the term "α-functionalized internal olefin" shall refer to an organic compound comprising a chain of carbon atoms having an internal carbon-carbon double bond (C=C) and having a functional substituent, such as a carboxylic acid or ester group, at one of the terminal carbon atoms. Preferred α-functionalized internal olefins may be represented by formula (1) hereinabove reproduced as follows:

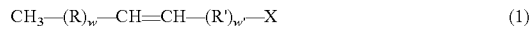

$$CH_3—(R)_w—CH=CH—(R')_{w'}—X \quad (1)$$

wherein R and R' are each independently selected from substituted or unsubstituted hydrocarbyl diradicals, preferably, substituted or unsubstituted aliphatic hydrocarbyl diradicals, more preferably, alkylene or alkylidene diradicals, most preferably, methylene (—$CH_2$—); w and w' are each independently a whole number ranging from 0 to about 20, preferably, from about 3 to about 12; and X is a polar functional group, preferably, a polar functional group selected from carboxylic acid, ester, formyl, and dialkylamide groups. Typically, R or R' each contains at least about 1 or 2 carbon atoms. If R or R' is substituted, the substituent(s) may comprise any group or groups that are substantially non-reactive in the metathesis process. Suitable substituents include, without limitation, $C_{1-20}$ alkyl, $C_{2-20}$ alkenyl, $C_{2-25}$ alkynyl, $C_{5-20}$ cycloalkyl, $C_{5-20}$ aryl, $C_{6-20}$ alkylaryl, $C_{6-20}$ arylalkyl, hydroxy, halo, ester, keto, ether, amide, and carbonate groups. More preferably, X is a carboxylic acid or an ester functionality; and the α-functionalized internal olefin comprises an unsaturated fatty acid or unsaturated fatty acid ester.

Non-limiting examples of suitable unsaturated fatty acids that may be used in the process of this invention include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (palmitoleic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21 triacontenoic (lumequeic) acids, as well as 2,4-hexadienoic (sorbic), cis-9-cis-12-octadecadienoic (linoleic), cis-9-cis-12-cis-15-octadecatrienoic (linolenic), cis-9-trans-11-trans-13-eleostearic, 12-hydroxy-cis-9-octadecenoic (ricinoleic), 4-oxo-trans-9-trans-11-trans-13-licanic, and like acids. Oleic acid or palmitoleic acid is most preferred. Unsaturated fatty acids can be obtained commercially or synthesized by saponifying fatty acid esters, saponification being known to those skilled in the art.

For the purposes of this invention, an unsaturated fatty acid ester is an ester product of an unsaturated fatty acid and an alcohol. The alcohol can be any monohydric, dihydric, or polyhydric alcohol that is capable of condensing with the unsaturated fatty acid to form the corresponding unsaturated fatty acid ester. Typically, the alcohol contains from 1 to about 20 carbon atoms ($C_{1-20}$), preferably, from 1 to about 12 carbon atoms ($C_{1-12}$), and more preferably, from 1 to about 8 carbon atoms ($C_{1-8}$). Preferably, the alcohol is a $C_{1-12}$ monoalkanol. A preferred ester is a methyl ester.

Suitable unsaturated fatty acid esters can be obtained by transesterification of plant and vegetable oils, including castor, olive, peanut, rapeseed, corn, sesame, cottonseed, soybean, sunflower, safflower, linseed, canola, palm, and like seed oils, as well as animal fats, such as whale oils. Oils exist in nature as the triglyceride esters of fatty acids. For the purposes of this invention, "transesterification of an oil" is defined as a process wherein glycerol of the triglyceride is replaced with a different alcohol, preferably, a lower monoalkanol, namely, a $C_{1-12}$ mono-alkanol. Process conditions and catalysts for the transesterification of oils are well known in the art. More preferably, the fatty acid ester is derived from a $C_{8-25}$ unsaturated fatty acid and a $C_{1-8}$ mono-alcohol. Even more preferably, the fatty acid ester is a $C_{8-25}$ unsaturated fatty acid methyl ester, more preferably, methyl oleate.

Further to the first step of this process invention, an α-olefinic monomer having three or more carbon atoms is required. As used herein, the term "α-olefin" shall refer to an organic compound comprising a chain of carbon atoms having a terminal carbon-carbon double bond (C=C). The term "monomer" shall refer to a molecule of single α-olefin, i.e., a form of lowest molecular weight; as contrasted, for example, with a "dimer" wherein two of the monomers are combined into a molecule of twice (or near twice) the molecular weight of the monomer. Generally, the α-olefinic monomer is not functionalized with polar groups, but may contain alkyl or other non-polar substituents along the carbon chain. Non-limiting examples of suitable α-olefinic monomers include propylene, 1-butene, 1-pentene, 1-hexene, 1-heptene, 1-octene, 1-nonene, 1-decene, and the like. A preferred α-olefinic monomer may be represented by formula (2) shown hereinabove and repeated as follows:

$$CH_2=CH-(R)_w-CH_3 \quad (2)$$

wherein R and w are as defined hereinbefore in connection with formula (1), and provided that each R and w in formula (2) is identical to the R and w selected for formula (1). Preferably, the α-olefinic monomer having three or more carbon atoms is a $C_{3-15}$ α-olefin. More preferably, the α-olefinic monomer having three or more carbon atoms is a $C_{6-12}$ α-olefin, and most preferably, either 1-octene or 1-decene. It should be appreciated by one skilled in the art that if R and w in formula (2) are not identical to R and w in formula (1), then the process of this invention is still valid and operable; but the process leads to additional olefinic products and additional separation requirements.

The α-functionalized internal olefin and the α-olefinic monomer having three or more carbon atoms may be fed to the first reaction zone in any amounts that provide for an operable metathesis process. Typically, the molar ratio of α-functionalized internal olefin to α-olefin having three or more carbon atoms is greater than about 0.05/1.0, preferably, greater than about 0.3/1.0. Typically, the molar ratio of α-functionalized internal olefin to α-olefin having three or more carbon atoms is less than about 2.0/1.0, preferably, less than about 1.3/1.0, and more preferably, less than about 1.0/1.0.

The first metathesis in step (a) in the first reaction zone can be started up with commercial feeds of the α-functionalized internal olefin and the α-olefinic monomer having three or more carbon atoms. While the α-functionalized internal olefin is a required feed, only a start-up quantity of the α-olefinic monomer having three or more carbon atoms is needed, for the reason that the overall process of this invention generates among other products the α-olefinic monomer having three or more carbon atoms. A portion of this α-olefinic monomer product may be removed for downstream utilities; but the balance of the α-olefinic monomer product is cycled back to the first reaction zone for use as feed to process step (a). Thus, whereas α-functionalized internal olefin is continuously consumed as a feed, only a start-up quantity of commercial α-olefinic monomer is required, the bulk of the α-olefinic monomer for step (a) being generated during the process of this invention. A suitable start-up quantity of α-olefinic monomer is any quantity that satisfies the range set forth hereinbefore of the molar ratio of α-functionalized internal olefin to α-olefin having three or more carbon atoms.

As an alternative start-up procedure in the special circumstance wherein the starting reactants are formulas (1) and (2) hereinabove, the first metathesis in the first reaction zone can be started up with a commercial feed of α-functionalized internal olefin absent the α-olefinic monomer having three or more carbon atoms. Homo-metathesis of the α-functionalized internal olefin produces unfunctionalized internal olefin, which in the second reaction zone produces α-olefinic monomer having three or more carbon atoms as a product. In this alternative embodiment, the process can be run for a time with only α-functionalized internal olefin fed to step (a), until the feed of α-olefin having three or more carbon atoms builds up to a useful quantity to sustain the process in the first reaction zone of step (a).

In some instances a liquid diluent may be desirably added to the reactant feed to step (a), although liquid diluents tend to increase recycle requirements and costs. A liquid diluent may be desirable, however, when the α-functionalized internal olefin and the α-olefin having three or more carbon atoms are not entirely miscible, that is, when they substantially do not exist as a one phase solution. The liquid diluent can be any thermally stable and chemically stable liquid that is also miscible with the reactant olefins. The term "thermally stable" means that the liquid diluent does not substantially decompose at the process temperature. The term "chemically stable" means that the liquid diluent is essentially non-reactive with the olefinic reactants and products; and also implies that the liquid diluent does not substantially coordinate with or bond to the metathesis catalyst in a manner that negatively impacts catalyst performance. The term "miscible" means that the liquid diluent and olefinic reactants form a homogeneous solution essentially without phase separation. Non-limiting examples of suitable liquid diluents include aromatic hydrocarbons, such as benzene, toluene, xylenes, and the like; chlorinated aromatic hydrocarbons, preferably chlorinated benzenes, such as chlorobenzene and dichlorobenzene; alkanes, such as pentane, hexane, cyclohexane, and the like; and chlorinated alkanes, such as methylene chloride and chloroform. The quantity of liquid diluent employed will depend upon the specific olefinic reactants and catalyst. One skilled in the art can readily determine an appropriate quantity of diluent. As a guideline, an amount of liquid diluent ranging from about 10 weight percent to about 100 weight percent, based on the weight of the α-functionalized internal olefin, may be suitably employed.

The α-functionalized internal olefin is usually fed to the reactor as a neat liquid or in a solution with the liquid diluent. The α-olefin having three or more carbon atoms may be fed to the reactor in a gas or liquid phase depending upon the boiling properties of the α-olefin and the operating conditions in the reactor. The metathesis process in the first reaction zone can be conducted under an inert gaseous atmosphere, so as to minimize interference by oxygen. Suitable inert atmospheres include, without limitation, helium, neon, argon, nitrogen, and mixtures thereof. More preferably, the metathesis process in the first reaction zone is conducted in a single liquid phase under sufficient hydrostatic pressure essentially to keep any reactant and product gases in solution.

As a further option, a stabilizing ligand may be added to the metathesis catalyst and/or process in the first reaction zone. The stabilizing ligand may be any molecule or ion that promotes catalyst stability in the metathesis process, as measured, for example, by increased activity or extended catalyst lifetime, as compared with a process run with identical reactants and an identical catalyst under identical process conditions but in the absence of stabilizing ligand. Non-limiting examples of stabilizing ligands include tri(alkyl)phosphines, such as tricyclohexylphosphine, tricyclopentylphosphine, and tributylphosphine; tri(aryl)phosphines, such as tri(phenyl)phosphine, tri(methylphenyl)phosphine (ortho, meta, and para substituted isomers), and tri(p-fluorophenyl)phosphine; diarylalkylphosphines, for example, diphenylcyclohexylphosphine; dialkylarylphosphines, such as dicyclohexylphenylphosphine; ethers, such as anisole; pyridines, such as 2,6-dimethylpyridine, 2-t-butylpyridine, 2,6-difluoropyridine, and 2-methylpyridine; phosphine oxides, such as triphenylphosphine oxide; as well as phosphinites, phosphonites, phorphoramidites, and mixtures of any of the aforementioned ligands. Preferably, the stabilizing ligand is a tri (alkyl)phosphine, more preferably, tri(cyclohexyl) phosphine. The quantity of stabilizing ligand can vary, however, depending upon the specific catalyst employed and its specific ligand components. Typically, the molar ratio of stabilizing ligand to catalyst is greater than about 0.05/1, and preferably, greater than about 0.5/1. Typically, the molar ratio of stabilizing ligand to catalyst is less than about 2.0/1, and preferably, less than about 1.5/1.

The first metathesis catalyst may be any compound or complex that is capable of facilitating a cross-metathesis reaction of the α-functionalized internal olefin with the α-olefin having three or more carbon atoms to form an α,ω-functionalized olefin. The catalyst may also promote homometathesis of the α-olefin having three or more carbon atoms to form an unsubstituted internal olefinic dimer, as described hereinafter. Suitable catalysts exhibit a tolerance to functional groups, such as carboxylic acid, ester, formyl, alcohol, and dialkylamide groups. Non-limiting examples of suitable catalysts include first-generation and second-generation Grubbs catalysts comprising ruthenium and osmium complexes, Hoveyda catalysts comprising ruthenium and osmium complexes, Schrock catalysts comprising molybdenum complexes, as known in the art and as disclosed in the following references, all incorporated herein by reference: M. Sholl, M., S. Ding, C. W. Lee, and R. H. Grubbs, *Organic Letters,* 1999, I, 953; Kingsbury, J., et al., *Journal of the American Chemical Society,* 1999, 121, pp. 791-799; W. A. Herrmann, et al., *Angewandte Chemie, International Edition,* 1995, 21, pp. 2371-2374; R. R. Schrock et al., *Journal of the American Chemical Society,* 1990, 112, pp. 3875-3886; WO 93/20111, U.S. Pat. No. 5,312,940, WO 96/04289; WO 00/43343; and WO 02/076920. A preferred metathesis catalyst comprises a ruthenium or osmium metathesis complex, more preferably, a first-generation or second-generation Grubbs ruthenium complex. A preferred form of the Grubbs catalysts may be represented by the following formula (6):

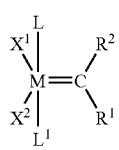

(6)

wherein M is ruthenium or osmium; $R^1$ and $R^2$ are independently selected from hydrogen or a hydrocarbon selected from the group consisting of $C_{2-20}$ alkenyl, $C_{2-20}$ alkynyl, $C_{1-20}$ alkyl, aryl, $C_{1-20}$ carboxylate, $C_{2-20}$ alkoxy, $C_{2-20}$ alkenyloxy, $C_{2-20}$ alkynyloxy, aryloxy, $C_{2-20}$ alkoxycarbonyl, $C_{1-20}$ alkylthio, $C_{1-20}$ alkylsulfonyl, and $C_{1-20}$ alkylsulfinyl; $X^1$ and $X^2$ are independently selected from any anionic ligand; and L and $L^1$ are independently selected from any neutral electron donor, preferably, phosphine, sulfonated phosphine, phosphite, phosphinite, phosphonite, arsine, stibine, ether, amine, amide, sulfoxide, carboxyl, nitrosyl, pyridine, and thioethers, most preferably, trialkylphosphine ligands where at least one of the alkyl groups is a secondary alkyl or a cycloalkyl group. Preferred examples of second-generation Grubbs catalysts include:

tricyclohexylphosphine[1,3-bis(2,4,6-trimethylphenyl)-4,5-dihydroimidazol-2-ylidene][benzylidene]ruthenium dichloride;

tricyclohexylphosphine[1,3-bis(2,4,6-trimethylphenyl)-4,5-dihydroimidazol-2-ylidene][benzylidene]ruthenium dibromide;

tricyclohexylphosphine[1,3-bis(2,4,6-trimethylphenyl)-4,5-dihydroimidazol-2-ylidene][benzylidene]ruthenium diiodide;

Other preferred catalysts comprise ruthenium complexes represented by formula (7):

(7)

In formula (7), M is Ru; each $L^2$ is independently selected from neutral and anionic ligands in any combination that balances the bonding and charge requirements of M; a is an integer, preferably from 1 to about 4, which represents the total number of ligands $L^2$; $R^3$ is selected from hydrogen, straight-chain or branched alkyl, cycloalkyl, aryl, and substituted aryl radicals; Y is an electron donor group of an element from Group 15 or 16 of the Periodic Table, (as referenced by the IUPAC in *Nomenclature of Inorganic Chemistry: Recommendations* 1990, G. J. Leigh, Editor, Blackwell Scientific Publications, 1990); Y being more preferably O, S, N, or P; each $R^4$ is independently selected from hydrogen, alkyl, cycloalkyl, aryl, and substituted aryl radicals sufficient to satisfy the valency of Y, preferably such that Y is formally neutral; b is an integer, preferably 0 to about 2, representing the total number of $R^4$ radicals; and Z is an organic diradical that is bonded to both Y and the carbene carbon (C) so as to form a bidentate ligand, which ligand in connection with the M atom forms a ring of from about 4 to about 8 atoms. More preferably, each $L^2$ in formula (7) is independently selected from the group consisting of halides (fluoride, chloride, bromide, and iodide); cyanide, thiocyanate, phosphines of the formula $PR^5_3$, amines of the formula $NR^5_3$, water and ethers of the formula $R^5OR^5$, thioethers of the formula $SR^5_2$, and ligands having the formulas (8) and (9) hereinafter:

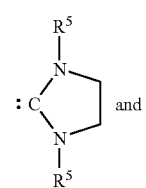

(8)

-continued

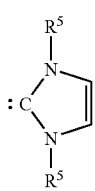
(9)

wherein each $R^5$ in any of the aforementioned formulas is independently selected from the group consisting of hydrogen, alkyl, preferably, $C_{1-15}$ alkyl; cycloalkyl, preferably, $C_{3-8}$ cycloalkyl; aryl, preferably, $C_{6-15}$ aryl, and substituted aryl, preferably $C_{6-15}$ substituted aryl, radicals. Mixtures of any of the aforementioned ligands $L^2$ may be employed in any given species of formula (7). More preferably, $R^3$ is selected from the group consisting of hydrogen, $C_{1-15}$ alkyl, $C_{3-8}$ cycloalkyl, and $C_{6-15}$ aryl radicals. More preferably, each $R^4$ is independently selected from the group consisting of $C_{1-15}$ alkyl, $C_{3-8}$ cycloalkyl, and $C_{6-15}$ aryl radicals. Preferably, Z is selected from the following diradicals: ethylene (10), vinylene (11), phenylene (12), substituted vinylenes (13), substituted phenylenes (14), naphthylene (15), substituted naphthylenes (16), piperazindiyl (17), piperidiyl (18):

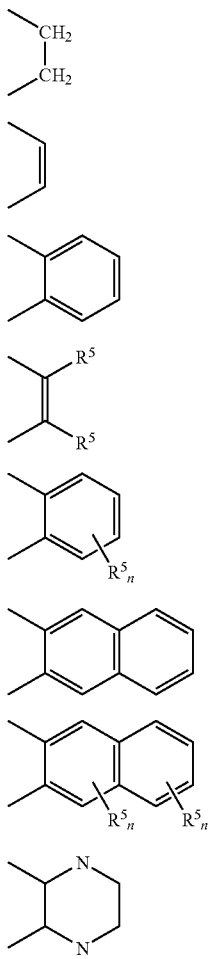

(10)
(11)
(12)
(13)
(14)
(15)
(16)
(17)

-continued

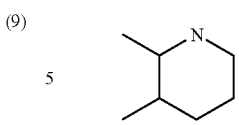
(18)

wherein each $R^5$ may be, as noted above, selected from hydrogen, alkyl, preferably, $C_{1-15}$ alkyl; cycloalkyl, preferably, $C_{3-8}$ cycloalkyl; and aryl, preferably, $C_{6-15}$ aryl, radicals; and wherein each n is an integer from 1 to about 4.

A more preferred embodiment of formula (7) may be represented by formula (19):

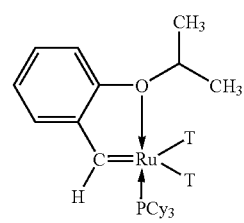
(19)

wherein each T is independently selected from Cl and Br, and $PCy_3$ is tricyclohexylphosphine.

Although the first metathesis catalyst for process step (a) comprises, preferably, a homogeneous catalyst (i.e., a catalyst dissolved in the liquid reaction mixture), the catalyst may alternatively be bound to or deposited on any conventional catalyst support, such as silica, alumina, silica-alumina, aluminosilicates, titania, titanosilicates, carbon, reticulated cross-linked polystyrenes, and the like. If a catalyst support is used, generally, the catalyst is loaded onto the support in an amount that is greater than about 0.01 weight percent catalytic metal, and preferably, greater than about 0.05 weight percent catalytic metal, based on the total weight of the catalyst plus support. Generally, the catalyst is loaded onto the support in an amount that is less than about 20 weight percent catalytic metal, and preferably, less than about 10 weight percent catalytic metal, based on the total weight of the catalyst and support.

The metathesis process in the first reaction zone can be conducted in any conventional reactor suitably designed to accommodate such as process. Preferably, the first reaction zone is run in the liquid phase only, as mentioned hereinbefore. Typically, the process temperature is greater than about −10° C., preferably, greater than about 0° C. Typically, the process temperature is less than about 150° C., preferably, less than about 120° C. Typically, the total pressure in the reactor is sufficient to maintain ethylene in the liquid phase without substantial bubbling. Preferably, the total pressure is greater than about 5 psig (34.5 kPa), more preferably, greater than about 100 psig (689 kPa), and most preferably, greater than about 200 psig (1,379 kPa). Preferably, the total pressure is less than about 1,000 psig (6,895 kPa) for design considerations.

When the process in the first reaction zone is conducted as described hereinabove, then two or more metathesis products are formed, including an α,ω-functionalized olefin, one or more unfunctionalized internal olefins of symmetrical or unsymmetrical form, and optionally, an α,ω-difunctionalized olefinic dimer. For the purposes of this invention, the term "α,ω-functionalized olefin" is defined as an organic compound comprising a chain of carbon atoms having a carbon-carbon double bond (C=C) at a terminal carbon atom and having a functionalized substituent, such as an ester or carboxylic acid group, on the terminal carbon at the opposite end of the chain. For the purposes of this invention, the term "unfunctionalized internal olefin" is defined as an organic compound comprising a chain of carbon atoms having a carbon-carbon double bond (C=C) at an internal position in the chain and having no functional groups at the ends of the chain. For the purposes of this invention, the term "α,ω-difunctionalized olefinic dimer" is defined as an organic compound comprising a chain of carbon atoms having an internal carbon-carbon double (C=C) bond and having a substituent, such as an ester or carboxylic acid group, on each of the terminal carbon atoms at both ends of the chain. Moreover, the two functional substituents are identical. As a preferred example, the metathesis of methyl oleate with 1-decene yields the cross-metathesis product methyl 9-decenoate and metathesis products 9-octadecene and, optionally, dimethyl 9-octadecen-1,18-dioate. Since these processes run to equilibrium, the product mixtures usually further comprise unconverted α-functionalized internal olefin and unconverted α-olefin having three or more carbon atoms.

Preferably, the α,ω-functionalized olefin may be represented by formula (3) hereinabove, reproduced as follows:

$$CH_2=CH-(R')_{w'}-X \quad (3)$$

In formula (3) R' is a substituted or unsubstituted hydrocarbyl diradical, preferably, a substituted or unsubstituted aliphatic hydrocarbyl diradical, more preferably, an alkylene or alkylidene diradical, most preferably, methylene (—CH$_2$—); w' is a whole number ranging from 0 to about 20, preferably, from about 3 to about 12; and X is a polar functional group, preferably, a polar functional group selected from carboxylic acid, ester, formyl, and dialkylamide groups; provided that each R', w', and X in formula (3) is identical to their respective counterpart selected in formula (1).

Preferably, the unfunctionalized internal olefin is an unfunctionalized internal olefinic dimer represented by formula (4) hereinabove, reproduced hereinafter:

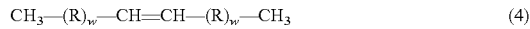

$$CH_3-(R)_w-CH=CH-(R)_w-CH_3 \quad (4)$$

In formula (4) each R is identical and is a substituted or unsubstituted hydrocarbyl diradical, preferably, a substituted or unsubstituted aliphatic hydrocarbyl diradical, more preferably, an alkylene or alkylidene diradical, most preferably, methylene (—CH$_2$—); each w is identical and is a whole number ranging from 0 to about 20, preferably, from about 3 to about 12; provided that each R and w in formula (4) is identical to its respective counterpart selected in formula (1). For the purposes of this invention, the term "unfunctionalized" means that the α,ω-terminal positions of the unfunctionalized internal olefin comprise methyl groups that are not substituted with any further functionality. In contrast, internal carbon positions of the unfunctionalized internal olefin, for example, represented by R in formula (4), are permitted to be substituted with a variety of substituents as noted hereinbefore.

Preferably, the α,ω-difunctionalized internal olefinic dimer may be represented by formula (5) hereinabove, reproduced as follows:

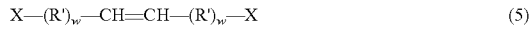

$$X-(R')_w-CH=CH-(R')_w-X \quad (5)$$

In formula (5) each R' is identical and is a substituted or unsubstituted hydrocarbyl diradical, preferably, a substituted or unsubstituted aliphatic hydrocarbyl diradical, more preferably, an alkylene or alkylidene diradical, most preferably, methylene (—CH$_2$—); each w' is identical and is a whole number ranging from 0 to about 20, preferably, from about 3 to about 12; and each X is identical and is a polar functional group, preferably, a polar functional group selected from carboxylic acid, ester, formyl, and dialkylamide groups; provided that each R', w', and X in formula (5) is also identical to its respective counterpart selected in formula (1). More preferably, X in the formulas is a carboxylic acid or ester functionality.

Optionally, at the conclusion of the first metathesis step (a), the metathesis catalyst can be removed from the resulting product effluent by any method known in the art for such metal removal. A preferred method is described in WO-A2-2004/037754, incorporated herein by reference, which teaches removal of a metathesis catalyst, and preferably, ruthenium, from a metathesis product effluent by contacting the effluent with an adsorbent, such as carbon, or alternatively, by distilling the product effluent in a short-path wiped film evaporator to obtain a distillate essentially devoid of catalytic metal. Conditions for the adsorbent method and the distillation method are presented in WO-A2-2004/037754.

In the second step of the process of this invention, the effluent stream from the first reactor, comprising the α,ω-functionalized olefin, the unfunctionalized internal olefin, unconverted α-functionalized internal olefin, unconverted α-olefin having three or more carbon atoms, and optional α,ω-difunctionalized internal olefin, is introduced into a first separation zone for separation into substantially pure streams of each constituent component present in the effluent. The first separation zone is conventional in design and may include distillation, extraction, extractive distillation, crystallization, and/or chromatographic methods, as may be applicable to the organic compounds being separated. One skilled in the art will know how to design such a separation means for the specific effluent to be separated.

A preferred embodiment of the first separation zone comprises a distillation train. Distillation of the metathesis product stream from the first reaction zone in a first distillation column produces a top stream comprising the α,ω-functionalized olefin and the unreacted α-olefinic monomer having three or more carbon atoms, and a bottoms stream comprising unreacted α-functionalized internal olefin, unfunctionalized internal olefin, and optionally, α,ω-difunctionalized internal olefinic dimer. The top stream is preferably processed in a second distillation column to recover the desired α,ω-functionalized olefin product stream and a first output stream of unconverted α-olefin having three or more carbon atoms, the latter of which is typically recycled at least in part back to the first metathesis reaction zone. The bottoms stream from the first distillation column is distilled in a third distillation column to recover an unconverted α-functionalized internal olefin stream, an unfunctionalized internal olefin stream, and if any, an α,ω-difunctionalized internal olefinic dimer stream. A portion of the unconverted α-functionalized internal olefin stream and a portion of the α,ω-difunctionalized internal olefinic dimer stream, if any, may be recycled to the first metathesis reactor of step (a). The quantities of recycled materials depend upon the mass balance and stoichiometry requirements of the metathesis process of the first metathesis reaction of step (a).

In an even more preferred embodiment wherein the metathesis reactants in the first reaction zone are methyl 9-octadecenoate and 1-decene, distillation of the metathesis product stream in a first distillation column produces a top stream comprising the desired product methyl 9-decenoate and the unreacted 1-decene, and a bottoms stream comprising methyl 9-octadecenoate, 9-octadecene, and if any, dimethyl 9-octadecen-1,18-dioate. The first distillation column can be suitably operated at a bottoms temperature greater than about 150° C. (423K) and less than about 252° C. (525K) and at a head pressure greater than about 0.13 KPa and less than about 6.6 kPa. The top stream is introduced into a second column and distilled to recover the product stream of methyl 9-decenoate and a first output 1-decene stream, the latter of which at least in part is recycled back to the first reaction zone. The second distillation column can be suitably operated at a temperature greater than about 75° C. (348K) and less than about 177° C. (450K) and at a head pressure greater than about 0.13 kPa and less than about 6.6 kPa. The bottoms stream from the first column is introduced into a third distillation column to recover an unconverted methyl oleate stream, a 9-octadecene stream, and if any, a dimethyl 9-octadecen-1,18-dioate stream. The third distillation column can be suitably operated at a temperature greater than about 150° C. (423K) and less than about 252° C. (525K) and at a pressure greater than about 0.13 kPa and less than about 6.6 kPa. Both unconverted methyl oleate and a portion of the dimethyl 9-octadecen-1, 18-dioate stream, if any, may be recycled to the first metathesis reactor of step (a). The amounts of recycle will depend upon the stoichiometry of the reaction scheme.

In the third step of this process invention, the unfunctionalized internal olefin, preferably comprising 9-octadecene, is introduced with an ethylene feed into a second metathesis reaction zone wherein the aforementioned olefin reactants are contacted with a second metathesis catalyst under reaction conditions sufficient to generate as a product α-olefinic monomer having three or more carbon atoms, preferably, 1-decene. The catalyst and process conditions suitable for the second metathesis step are similar to those used in the prior art for olefin disproportionation or ethenolysis, as described, for example, in U.S. Pat. No. 3,647,906 and U.S. Pat. No. 3,261,879 (Philips triolefin process), incorporated herein by reference. Reference is also made to a more recent process, namely ABB Lummus Global Olefin Conversion Technology (OCT), known to those of skill in the art, as disclosed in *European Chemical News*, Week of Mar. 25-31, 2002, pp. 20-21.

Generally, the catalyst for the ethenolysis may be any conventional heterogeneous or homogeneous metathesis catalyst that promotes the formation of desired α-olefinic monomer having three or more carbon atoms. Desirably, the catalyst minimizes ethylene oligomerization and homo-metathesis of the unfunctionalized internal olefin. Suitable catalysts include, but are not limited to, rhenium oxides supported on alumina, optionally pre-treated with alkali or alkaline earth metal compounds; molybdenum oxides and/or cobalt oxides supported on alumina; and tungsten oxides supported on silica, as disclosed, for example, in U.S. Pat. No. 3,261,879 and U.S. Pat. No. 3,647,906, incorporated herein by reference. For the purposes of this invention, Grubbs catalysts, such as those disclosed in WO 96/04289 and WO 02/083742, are typically not used in the ethenolysis step. Suitable process conditions for the ethenolysis are also disclosed in the art. Specifically, the molar ratio of ethylene to unfunctionalized internal olefin typically may range from about 0.4:1 to about 10:1. The process temperature of the ethenolysis is typically greater than about 120° C. Typically, the process temperature less than about 210° C. The process pressure is typically greater than about 300 psig (2,068 kPa). The process pressure is typically less than about 525 (3,619 kPa).

In the fourth step of this process invention, the effluent from the second reaction zone (ethenolysis) is fed to a second separation zone of conventional design for separating the effluent stream comprising α-olefinic monomer having three or more carbon atoms, unconverted ethylene, and unconverted unfunctionalized internal olefin. Typically, the second separation zone comprises at least one distillation column from which a top stream of unconverted ethylene is obtained, which typically is recycled to the second metathesis reactor for feed to the ethenolysis reaction. Typically, the distillation yields a fraction comprising a second output α-olefinic monomer stream, the monomer having three or more carbon atoms; while a bottom fraction is recovered comprising unfunctionalized internal olefin which is typically recycled to the second reaction zone for further ethenolysis. Optionally, a portion of the second output stream comprising α-olefinic monomer having three or more carbon atoms may be removed as product; the balance may be cycled to the first metathesis reaction zone, the cycled portion depending upon the process stoichiometry in the first metathesis reaction zone. In a preferred embodiment, the feed to the second separation zone comprises 1-decene, unconverted ethylene, and unconverted 9-octadecene. The normal boiling point (at 1 atm, 101 kPa) of ethylene is −104° C.; of 1-decene is 229° C.; and of octadecene is estimated to be about 313° C.; therefore, the fractional distillation of a mixture thereof is well within the skill of the design engineer.

The following examples are provided as illustrations of the process of this invention, but should not be construed as limiting the invention in any manner. In light of the disclosure herein, those of skill in the art will recognize modifications of the process that fall within the scope of this invention.

Example 1

The following procedure was employed to evaluate the feasibility of cross-metathesizing methyl oleate with 1-decene. Methyl oleate (Aldrich) was degassed and purified over a column of alumina. An amount of alumina was employed equal to 50 percent of the weight of the methyl oleate. In a dry box, the purified and degassed methyl oleate (6.0147 g, 20.1 mmol) and 1-decene (6.2770 g, 40.3 mmol) were combined with tetradecane (1.0549 g, internal standard) and a stir bar in a heavy walled glass reactor (Ace #8648-135), which was capped with a rubber septum. Tricyclohexylphosphine[1,3-bis-(2,4,6-trimethylphenyl)-2-imidazolidinylidene]benzylidene ruthenium(IV) dichloride (1.16 mg, 0.00125 mmol), a Grubbs catalyst, was dissolved in toluene (2.50 mL) and the resulting catalyst solution (0.25 mL; 0.000116 mmol catalyst) was loaded in a gas tight syringe and capped. The molar ratio of methyl oleate to 1-decene was 1/2. Both the reactor and syringe were removed from the glove box to a laboratory bench. The catalyst solution was added in one portion to the reactor through the septum. The cap was removed and the reactor was quickly connected to an ethylene/nitrogen dual manifold and flushed three times with nitrogen (55 psig, 379 kPa), then pressurized to 30 psig (207 kPa) under dynamic nitrogen pressure. The reactor was then placed over a magnetic stirrer and heated to 60° C. The reaction was monitored by sampling at reaction pressure via an shut-off valve through a 0.01" inner-diameter tube inserted into the reaction. A single sample (~100 μL) at 33 hours reaction time was quenched under pressure into a vial containing excess butyl vinyl ether. Conversion and selectivity were determined using gas chromatography analysis. For this sample the concentration of diester product was below the detection limit of the detection method. Results are set forth in Table 1 as Example 1b. All entries in the table are given as mole percentages. The conversion (CONV) of methyl oleate and selectivity (SEL) to specific products are calculated as follows, all compounds being expressed as moles.

CONV methyl oleate=100×[(methyl oleate$_{initial}$−methyl oleate$_{final}$)÷(methyl oleate$_{initial}$)]

SEL Compound A=100×[(Compound A)÷(Sum of all compounds containing the same functional group)]

MDEC$_{SEL}$=100×((MDEC+isoMDEC)÷(MDEC+isoMDEC+2*(c-DIESTER+t-DIESTER)))

DIESTER$_{SEL}$=100×((c-DIESTER+t-DIESTER)÷(c-DIESTER+t-DIESTER+0.5*(MDEC+isoMDEC)))

OCTADECENE$_{SEL}$=100×((t-OCTA+c-OCTA)÷(t-OCTA+c-OCTA+iso-OCTA+0.5*((DEC$_I$−DEC$_F$)+(iso DEC$_I$−iso DEC$_F$))))

Where:

MDEC is methyl 9-decenoate;

isoMDEC is isomerized methyl 9-decenoate i.e. methyl 8-decenoate;

c-DIESTER is cis diester;

t-DIESTER is trans diester;

c-OCTA is cis octadecene;

t-OCTA is trans octadecene;

iso-OCTA is an unidentified isomer of octadecene as found in the GC;

DEC$_I$ is decene initial moles;

DEC$_F$ is decene final moles;

isoDEC$_I$ is isodecene or 2-decene initial moles;

isoDEC$_F$ is isodecene or 2-decene final moles.

TABLE 1

Selectivity vs. Mole Ratio of Methyl Oleate to 1-Decene Charged

| Expt. | MO/1-Decene Charged | TON | Selectivity | | | MO Conversion |
|---|---|---|---|---|---|---|
| | | | Methyl Decenoate | Diester | Octadecene | |
| 1a | 1/1 | 68,000 | 72% | 27% | 60% | 45% |
| 1b | 1/2 | 71,000 | 100% | 0% | 49% | 48% |
| 1c | 2/1 | 97,000 | 51% | 49% | %73 | 57% |

1. MO = methyl oleate; TON = turnover number (moles of MO converted per mole of catalyst)

The aforementioned example was repeated twice using a molar ratio of methyl oleate to 1-decene of 1/1 (Example 1a) and then a molar ratio of 2/1 (Example 1c), with the results also presented in Table 1.

From Table 1, we observe a change in selectivity as the molar ratio of methyl oleate to 1-decene changes. At the 1/1 molar ratio methyl oleate to 1-decene, diester is formed in a significantly lower amount as compared with octadecene and methyl decenoate. At a 1/2 molar ratio of methyl oleate to 1-decene, the process is significantly more selective towards methyl decenoate. At a 2/1 molar ratio of methyl oleate to 1-decene, significant amounts of methyl oleate homo-metathesis products are formed, including octadecene and the diester.

This experiment illustrates step (a) of the invention and the feasibility of cross-metathesizing an α-functionalized internal olefin with an α-olefin having three or more carbon atoms in the presence of a homogeneous ruthenium metathesis catalyst, specifically, a Grubbs catalyst, to prepare an α,ω-functionalized olefin with improved catalyst turnover number. By comparison, if the α-functionalized internal olefin (methyl oleate) had been metathesized directly with ethylene in the presence of the identical catalyst under identical process conditions, the catalyst turnover number would have been less than about 10,000.

Example 2

Figure 2:
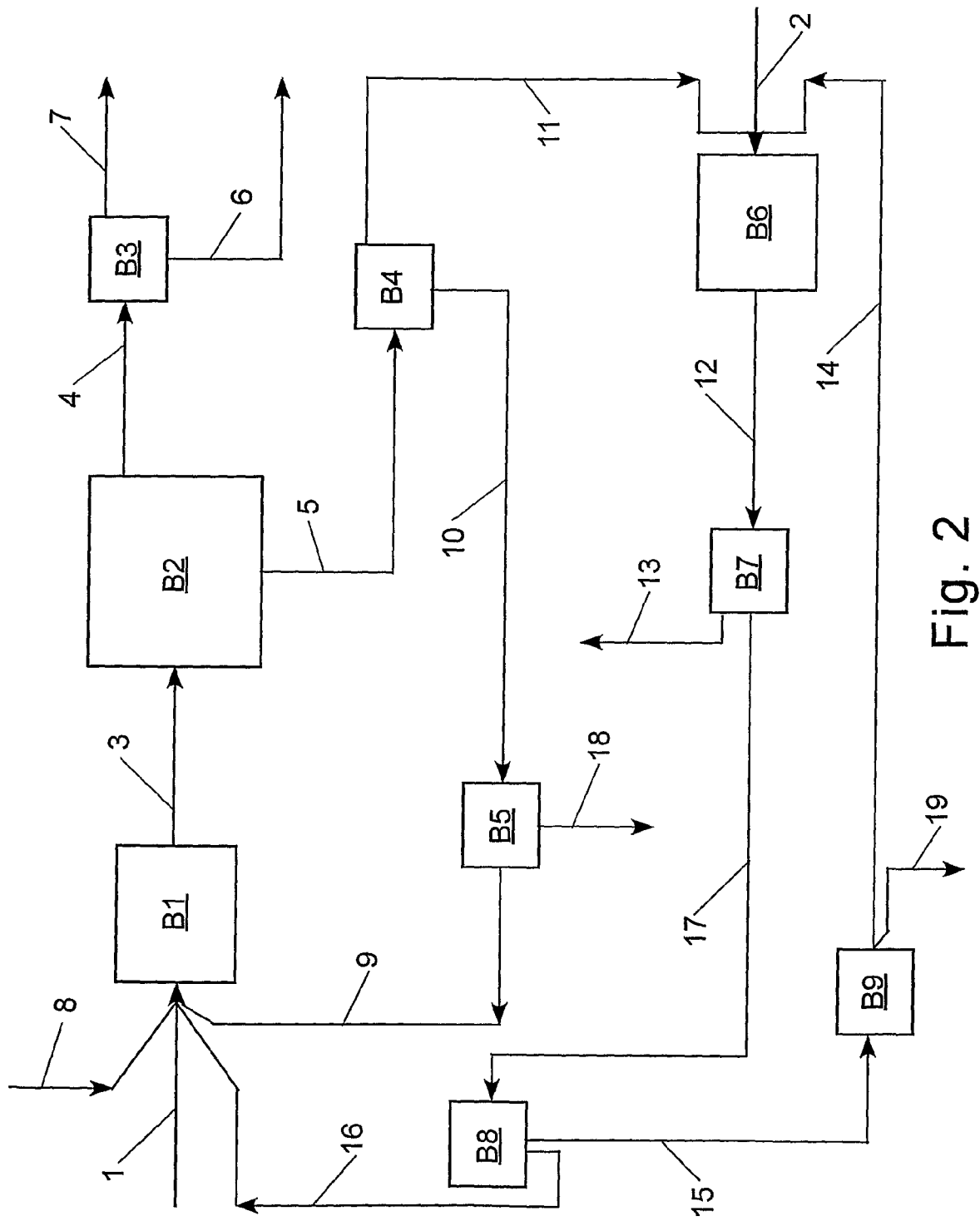
FIG. 2 illustrates a preferred embodiment of this invention for preparing methyl-9-decenoate and co-product 1-decene as illustrated for the input and output streams set forth in Table 2.

With reference to Table 2 and FIG. 2, the claimed process was simulated using an ASPEN® software program (Aspen Technology, Inc., 10 Canal Park, Cambridge, Mass. 02141, USA) for the following preferred embodiment: step (a) the cross-metathesis of methyl oleate and 1-decene; step (b) separation of the output stream from step (a) into a stream comprising methyl decenoate, a stream comprising 9-octadecene, a stream comprising unconverted methyl oleate, and a stream comprising unconverted 1-decene; step (c) the cross-metathesis of 9-octadecene with ethylene; step (d) separation of the output stream from step (c) into a stream comprising 1-decene, a stream comprising unconverted ethylene, and a stream comprising unconverted 9-octadecene. The physical properties of ethylene, 1-decene, and methyl oleate were taken from the ASPEN® database; however, the ASPEN® database does not contain information on methyl decenoate, 9-octadecene, and dimethyl 9-octadecen-1,18-dioate. Consequently, the following assumptions were made. 2-Ethylhexylacrylate was substituted for methyl decenoate. 1-Octadecene was substituted for 9-octadecene. These substitutions were based on the substitutes having similar functional group(s) (i.e., ester), identical molecular weights, and an identical number of double bonds. No component in the ASPEN® database matched dimethyl 9-octadecene-1,18-dioate; therefore, the structure of the diester was presented to the ASPEN® program with a query to estimate its physical properties.

In addition to the above, we have assumed that the metathesis processes are at equilibrium; accordingly, the above assumptions have essentially no impact on the metathesis reactor outlet compositions. The above assumptions do affect the distillation conditions. For each distillation, a distillation column having 20 theoretical stages was assumed. According to our simulation, normal boiling points, taken at 1 atm pressure (101 kPa), were as follows: Ethylene, −104° C.; 1-Decene, 171° C.; Methyl decenoate, 216° C.; Octadecene, 313° C. (assumed from substitute); Methyl oleate, 344° C. (assumed from substitute); Dimethyl 9-octadecen-1,18-dioate, 387° C. (estimated by ASPEN® software program). Process conditions, including temperature, pressure, and mass flow rates, as well as the composition of the input and output streams are shown in Table 2 with corresponding illustration in FIG. 2. In FIG. 2, unit B1 represents the first metathesis zone; unit B6 represents the second metathesis zone; units, B2, B3, B4, B7, and B8 represent distillation columns; and units B5 and B9 represent bleed off valves. From the simulation illustrated in Table 2, we have validated the overall process comprising two metathesis steps and two separation steps.

TABLE 2[1]

| | Streams | | | | | | | | | |
|---|---|---|---|---|---|---|---|---|---|---|
| | 1 | 2 | 3 | 4 | 5 | 6 | 7 | 8 | 9 | 10 |
| Temperature K | 298.1 | 303.1 | 333.1 | 363.3 | 498.3 | 401.7 | 349.6 | 303.1 | 500.4 | 500.4 |
| (°C.) | (25.0) | (29.9) | (60.0) | (90.3) | (225.3) | (128.7) | (76.6) | (30.0) | (227.4) | (227.4) |
| Pressure kPa | 790.8 | 689.5 | 517.1 | 5.3 | 7.9 | 6.5 | 4.0 | 689.5 | 6.5 | 6.5 |
| Total Mass Flow kg/sec | 3.196 | 0.46 | 11.571 | 5.09 | 6.5 | 1.950 | 3.143 | 1.767 | 3.750 | 3.788 |
| Mass Flow kg/sec | | | | | | | | | | |
| Ethylene | 0 | 0.46 | 0 | 0 | 0 | 0 | 0 | 0 | 0 | 0 |
| 1-Decene | 0 | 0 | 3.124 | 3.124 | Tr | Tr | 3.124 | 1.767 | Tr | Tr |
| Methyl Oleate | 3.196 | 0 | 2.334 | Tr | 2.334 | 0 | 0 | 0 | 2.311 | 2.334 |
| Methyl Decenoate | 0 | 0 | 1.972 | 1.970 | 0.002 | 1.950 | 0.020 | 0 | <.001 | <.001 |
| 9-Octadecene | 0 | 0 | 4.141 | Tr | 4.141 | 0 | 0 | 0 | 1.439 | 1.454 |
| Dimethyl 9-Octadecen-1,18-dioate | 0 | 0 | Tr | 0 | 0 | 0 | 0 | 0 | 0 | 0 |

| | Streams | | | | | | | | |
|---|---|---|---|---|---|---|---|---|---|
| | 11 | 12 | 13 | 14 | 15 | 16 | 17 | 18 | 19 |
| Temperature K | 479.4 | 298.1 | 298.1 | 458.5 | 458.5 | 361.1 | 298.1 | 500.4 | 458.5 |
| (°C.) | (206.4) | (25.0) | (25.0) | (185.5) | (185.5) | (88.1) | (25.0) | (227.4) | (185.5) |
| Pressure kPa | 5.3 | 517.1 | 5171.0 | 9.2 | 9.2 | 6.7 | 517.2 | 6.5 | 9.2 |
| Total Mass Flow kg/sec | 2.690 | 4.215 | 0.174 | 1.066 | 1.184 | 2.857 | 4.041 | 0.038 | 0.118 |
| Mass Flow kg/sec | | | | | | | | | |
| Ethylene | 0 | 0.171 | 0.174 | 0 | 0 | 0 | 0 | 0 | 0 |
| 1-Decene | Tr | 2.886 | 0 | 0.026 | 0.029 | 2.857 | 2.886 | Tr | 0.003 |
| Methyl Oleate | <.001 | 0.011 | 0 | 0.010 | 0.011 | Tr | 0.011 | 0.023 | 0.001 |
| Methyl Decenoate | 0.002 | 0.015 | 0 | 0.013 | 0.015 | Tr | 0.015 | Tr | 0.001 |
| 9-Octadecene | 2.687 | 1.129 | 0 | 1.016 | 1.129 | Tr | 1.129 | .015 | 0.113 |
| Dimethyl 9-octadecen-1,18-dioate | 0 | <.001 | 0 | <.001 | <.001 | Tr | <.001 | | |

[1]Tr = trace

What is claimed is:

1. A process of preparing an α,ω-functionalized olefin and a co-product α-olefin comprising:
   (a) contacting in a first reaction zone an α-functionalized internal olefin and an α-olefinic monomer having three or more carbon atoms in the presence of a first metathesis catalyst under reaction conditions sufficient to prepare a first effluent stream comprising an α,ω-functionalized olefin, an unfunctionalized internal olefin, unconverted α-functionalized internal olefin, and unconverted α-olefinic monomer having three or more carbon atoms, and optionally, α,ω-difunctionalized internal olefinic dimer;
   (b) introducing the first effluent stream from step (a) into a first separation zone and recovering therefrom an α,ω-functionalized olefin stream, an unfunctionalized internal olefin stream, an unconverted α-functionalized internal olefin stream, a first output α-olefinic monomer stream, the monomer having three or more carbon atoms, and optionally, an α,ω-difunctionalized internal olefinic dimer;
   (c) contacting in a second reaction zone a portion of the unfunctionalized internal olefin stream with ethylene in the presence of a second metathesis catalyst under reaction conditions sufficient to prepare a second effluent stream comprising α-olefinic monomer having three or more carbon atoms, unconverted unfunctionalized internal olefin, and unconverted ethylene;
   (d) introducing the second effluent stream from step (c) into a second separation zone under conditions sufficient to obtain a second output α-olefinic monomer stream, the monomer having three or more carbon atoms, an unconverted ethylene stream, and an unconverted unfunctionalized internal olefin stream; and
   (e) removing a portion of the first and/or second output α-olefinic monomer stream as product and cycling the balance of the first and second output α-olefinic monomer streams to the first reaction zone in step (a).

2. The process of claim 1 wherein the α-functionalized internal olefin is represented by the following formula:

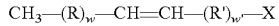

$$CH_3\text{---}(R)_w\text{---}CH\text{==}CH\text{---}(R')_{w'}\text{---}X$$

wherein R and R' are each independently a substituted or unsubstituted hydrocarbyl diradical; w and w' are each independently a whole number ranging from 0 to about 20; and X is a polar functional group selected from carboxylic acid, ester, aldehyde, and dialkylamide groups.

3. The process of claim 2 wherein the α-functionalized internal olefin is an unsaturated fatty acid or an unsaturated fatty acid ester.

4. The process of claim 3 wherein the α-functionalized internal olefin is selected from oleic acid or palmitoleic acid, or an ester of oleic or palmitoleic acid.

5. The process of claim 2 wherein the α-olefinic monomer having three or more carbon atoms is represented by the formula:

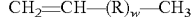

$$CH_2\text{==}CH\text{---}(R)_w\text{---}CH_3$$

wherein R is a substituted or unsubstituted hydrocarbyl diradical; and wherein w is a whole number ranging from 0 to about 20; provided that each R and w in the above formula is identical to R and w selected in the formula of claim 2.

6. The process of claim 5 wherein the α-olefinic monomer having three or more carbon atoms is 1-decene or 1-octene.

7. The process of claim 2 wherein the α,ω-functionalized olefin is represented by the following formula:

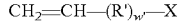

$$CH_2\text{==}CH\text{---}(R')_{w'}\text{---}X$$

wherein R' is a substituted or unsubstituted hydrocarbyl diradical; w' is a whole number ranging from 0 to about 20; and X is a polar functional group selected from carboxylic acid, ester, aldehyde, and dialkylamide moieties; provided that each R', w', and X in the above formula is identical to R', w', and X selected in the formula of claim 2.

8. The process of claim 7 wherein the α,ω-functionalized olefin is methyl 9-decenoate.

9. The process of claim 2 wherein the unfunctionalized internal olefin is an unfunctionalized internal olefinic dimer represented by formula:

wherein each R is identical and is a substituted or unsubstituted hydrocarbyl diradical; and each w is identical and is a whole number ranging from 0 to about 20; provided that each R and w in the above formula is identical respectively to the R and w selected in the formula of claim 2.

10. The process of claim 9 wherein the unfunctionalized internal olefinic dimer is 9-octadecene.

11. The process of claim 2 wherein the difunctional internal olefinic dimer is represented by the formula:

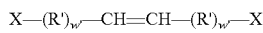

wherein each R' is identical and is a substituted or unsubstituted hydrocarbyl diradical; each w' is identical and is a whole number ranging from 0 to about 20; and each X is identical and is a polar functional group selected from carboxylic acid, ester, aldehyde, and dialkylamide groups; provided that each R', w' and X in the above formula is identical to R', w' and X selected in the formula of claim 2.

12. The process of claim 11 wherein the difunctional internal olefinic dimer is dimethyl 9-octadecen-1,18-dioate.

13. The process of claim 1 wherein the metathesis process in the first reaction zone of step (a) is conducted essentially in a liquid phase at a temperature greater than −10° C. and less than 150° C., and at a total pressure greater than 5 psig (34.5 kPa) and less than 1,000 psig (6,895 kPa).

14. The process of claim 1 wherein the first metathesis catalyst is represented by the formula:

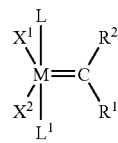

wherein M is ruthenium or osmium; $R^1$ and $R^2$ are each independently selected from hydrogen or a hydrocarbon selected from the group consisting of $C_{2-20}$ alkenyl, $C_{2-20}$ alkynyl, $C_{1-20}$ alkyl, aryl, $C_{1-20}$ carboxylate, $C_{2-20}$ alkoxy, $C_{2-20}$ alkenyloxy, $C_{2-20}$ alkynyloxy, aryloxy, $C_{2-20}$ alkoxycarbonyl, $C_{1-20}$ alkylthio, $C_{1-20}$ alkylsulfonyl, and $C_{1-20}$ alkylsulfinyl; $X^1$ and $X^2$ are independently selected from any anionic ligand; and L and $L^1$ are independently selected from phosphine, sulfonated phosphine, phosphite, phosphinite, phosphonite, arsine, stibine, ether, amine, amide, sulfoxide, carboxyl, nitrosyl, pyridine, and thioethers.

15. The process of claim 1 wherein the first metathesis catalyst is represented by the formula:

wherein M is Ru; each $L^2$ is independently selected from neutral and anionic ligands in any combination that balances the bonding and charge requirements of M; a is an integer, preferably from 1 to about 4, which represents the total number of ligands $L^2$; $R^3$ is selected from hydrogen, straight-chain or branched alkyl, cycloalkyl, aryl, and substituted aryl radicals; Y is an electron donor group of selected from O, S, N, or P; each $R^4$ is independently selected from hydrogen, alkyl, cycloalkyl, aryl, and substituted aryl radicals sufficient to satisfy the valency of Y such that Y is formally neutral; b is an from 0 to about 2, representing the total number of $R^4$ radicals; and Z is an organic diradical that is bonded to both Y and the carbene carbon (C) so as to form a bidentate ligand, which ligand in connection with the M atom forms a ring of from about 4 to about 8 atoms.

16. The process of claim 15 wherein each $L^2$ is independently selected from the group consisting of halides, cyanide, thiocyanate, phosphines of the formula $PR^5_3$, amines of the formula $NR^5_3$, water and ethers of the formula $R^5OR^5$, thioethers of the formula $SR^5_2$, and ligands having the formulas hereinafter:

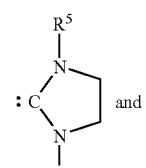

and

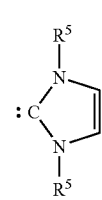

wherein each $R^5$ in any of the aforementioned formulas is independently selected from the group consisting of hydrogen, $C_{1-15}$ alkyl; $C_{3-8}$ cycloalkyl; $C_{6-15}$ aryl, and $C_{6-15}$ substituted aryl radicals; wherein $R^3$ is selected from the group consisting of hydrogen, $C_{1-15}$ alkyl, $C_{3-8}$ cycloalkyl, and $C_{6-15}$ aryl radicals; wherein $R^4$ is independently selected from the group consisting of $C_{1-15}$ alkyl, $C_{3-8}$ cycloalkyl, and $C_{6-15}$ aryl radicals; and wherein Z is selected from the following diradicals: ethylene, vinylene, phenylene, substituted vinylenes, substituted phenylenes, naphthylene, substituted naphthylenes, piperazindiyl, piperidiyl.

17. The process of claim 1 wherein the metathesis process in the first reaction zone employs a catalyst selected from the group consisting of tricyclohexylphosphine[1,3-bis(2,4,6-trimethylphenyl)-4,5-dihydroimidazol-2-ylidene][benzylidene]ruthenium dichloride;

tricyclohexylphosphine[1,3-bis(2,4,6-trimethylphenyl)-4,5-dihydroimidazol-2-ylidene][benzylidene]ruthenium dibromide; and
tricyclohexylphosphine[1,3-bis(2,4,6-trimethylphenyl)-4,5-dihydroimidazol-2-ylidene][benzylidene]ruthenium diiodide.

18. The process of claim 1 wherein the metathesis process in the second reaction zone of step (c) is conducted at a temperature greater than 120° C. and less than 210° C., and at a total pressure greater than 300 psia (2,068 kPa) and less than 523 psig (3,606 kPa).

19. The process of claim 1 wherein the metathesis process in the second reaction zone of step (c) employs a heterogeneous catalyst selected from rhenium oxides supported on alumina, optionally, promoted with one or more alkali or alkaline earth metal salts; molybdenum oxide supported on alumina; cobalt oxide supported on alumina; and tungsten oxide supported on silica.

20. The process of claim 1 wherein the unconverted α-functionalized internal olefin, and optionally, a portion of the α,ω-difunctionalized internal olefinic dimer, obtained from the first separation zone are recycled to the first reaction zone of step (a).

21. The process of claim 1 wherein unconverted α-olefinic monomer having three or more carbon atoms obtained from the first separation zone is recycled to the first reaction zone of step (a).

22. The process of claim 1 wherein the unconverted ethylene and a portion of the unconverted unfunctionalized internal olefin, both being obtained from the second separation zone, are recycled to the second reaction zone of step (c).

23. The process of claim 1 wherein the α-functionalized internal olefin is represented by the formula:

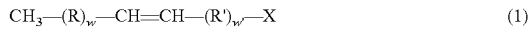
$$CH_3-(R)_w-CH=CH-(R')_{w'}-X \qquad (1)$$

wherein the α-olefinic monomer having three or more carbon atoms is represented by the formula:

$$CH_2=CH-(R)_w-CH_3 \qquad (2)$$

wherein the α,ω-functionalized olefin is represented by the formula:

$$CH_2=CH-(R')_{w'}-X \qquad (3)$$

wherein the unfunctionalized internal olefin is represented by the formula:

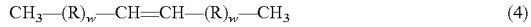
$$CH_3-(R)_w-CH=CH-(R)_w-CH_3 \qquad (4)$$

and wherein the α,ω-difunctionalized internal olefinic dimer is represented by the formula:

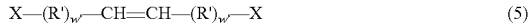
$$X-(R')_{w'}-CH=CH-(R')_{w'}-X \qquad (5)$$

wherein R and R' are each independently selected from hydrocarbyl diradicals; w and w' are each independently a whole number ranging from 0 to about 20; and X is a polar functional group selected from carboxylic acid, ester, formyl, and dialkylamide groups; provided that in formulas (2), (3), (4) and (5), each R, R', w, w', and X is identical to the corresponding group or number selected in formula (1).

24. A process of preparing methyl 9-decenoate and 1-decene comprising:
  (a) contacting in a first reaction zone methyl 9-octadecenoate (methyl oleate) and 1-decene in the presence of a ruthenium metathesis catalyst under reaction conditions sufficient to prepare a first effluent stream comprising methyl 9-decenoate, 9-octadecene, unconverted methyl 9-octadecenoate, unconverted 1-decene, and optionally, dimethyl 9-octadecen-1,18-dioate;
  (b) introducing the first effluent stream from step (a) into a first separation zone and recovering therefrom a methyl 9-decenoate stream, a 9-octadecene stream, an unconverted methyl 9-octadecenoate stream, a first output 1-decene stream, and optionally, dimethyl 9-octadecen-1,18-dioate,;
  (c) contacting in a second reaction zone a portion of the 9-octadecene stream with ethylene in the presence of a second metathesis catalyst selected from rhenium oxide supported on alumina, optionally, comprising alkali or alkaline earth metal compounds, molybdenum oxide supported on alumina, cobalt oxide supported on alumina, and tungsten oxide supported on silica, under reaction conditions sufficient to prepare a second effluent stream comprising 1-decene, unconverted 9-octadecene and unconverted ethylene;
  (d) introducing the second effluent stream from step (c) into a second separation zone under conditions sufficient to obtain a second output 1-decene stream, an unconverted ethylene stream, and an unconverted unfunctionalized internal olefin stream; and
  (e) removing a portion of the first and/or second output 1-decene streams as product and cycling the balance of the first and second 1-decene streams to the first reaction zone in step (a).

25. The process of claim 1 wherein the α-functionalized internal olefin is methyl 9-hexadecenoate (methyl palmitoleate); the α-olefin having three or more carbon atoms is 1-octene; the α,ω-functionalized olefin is methyl 9-decenoate; the unfunctionalized internal olefin is 7-tetradecene; and the α,ω-difunctionalized internal olefinic dimer is dimethyl 9-octadecene-1,18-dioate.

* * * * *